United States Patent [19]

Schlecht et al.

[11] 4,242,187

[45] Dec. 30, 1980

[54] PREPARATION OF ALKANES SUBSTITUTED BY CHLORINE ATOMS AND/OR SULFOCHLORIDE GROUPS

[75] Inventors: Helmut Schlecht, Ludwigshafen; Volkmar Weberndoerfer, Mannheim; Rudi Widder, Leimen, all of Fed. Rep. of Germany

[73] Assignee: BASF Aktiengesellschaft, Fed. Rep. of Germany

[21] Appl. No.: 8,156

[22] Filed: Jan. 31, 1979

[30] Foreign Application Priority Data

Feb. 9, 1978 [DE] Fed. Rep. of Germany ....... 2805441

[51] Int. Cl.³ .............................................. B01J 1/10
[52] U.S. Cl. .......................... 204/162 SH; 204/163 R
[58] Field of Search ...................... 204/162 SH, 163 R

[56] References Cited

U.S. PATENT DOCUMENTS

| | | | |
|---|---|---|---|
| 3,402,114 | 9/1968 | Hutson, Jr. et al. | 204/163 R |
| 3,911,004 | 10/1975 | Hertel et al. | 204/163 R |

FOREIGN PATENT DOCUMENTS 2459159  6/1976  Fed. Rep. of Germany.

OTHER PUBLICATIONS

Ullmanns Encyclopädie der Technischen Chemie, vol. 5 (1954) pp. 435, 437, 438 and 448.
Ullmanns Encyclopädie der Technischen Chemie, vol. 8 (1957) pp. 353 to 356.
Ullmans Encyclopädie der Technischen Chemie, vol. 16 (1965) pp. 562 and 563.
Lindner, Tenside-Textilhilfsmittel-Waschrohstoffe, 2nd Ed., vol. 1, pp. 708 to 713 (1964).

*Primary Examiner*—Leland A. Sebastian
*Attorney, Agent, or Firm*—Keil & Witherspoon

[57] ABSTRACT

Alkanes substituted by chlorine atoms and/or sulfochloride groups are prepared by reacting alkanes with chlorine, with or without sulfur dioxide, in a particular throughput ratio, in a reaction chamber inclined to the horizontal, the starting materials being passed through the reaction chamber in co-current, from below. The substituted alkanes or paraffins obtainable by the process of the invention are pesticides, plasticizers, solvents and starting materials for the preparation of such products, as well as of fat liquors, detergents, lubricating oils, synthetic resins and slip agents.

18 Claims, 2 Drawing Figures

PREPARATION OF ALKANES SUBSTITUTED BY CHLORINE ATOMS AND/OR SULFOCHLORIDE GROUPS

The present invention relates to a process for the preparation of alkanes which are substituted by chlorine atoms and/or sulfochloride groups, by reacting alkanes with chlorine, with or without sulfur dioxide, in a particular throughput ratio, in a reaction chamber inclined to the horizontal, the starting materials being passed through the reaction chamber in co-current, from below, and the reaction chamber being irradiated, in the lower part, with light having wavelengths of from 500 to 700 nanometers and in the upper part with light having wavelengths of from 200 to 500 nanometers.

Ullmanns Encyklopädie der technischen Chemie, Volume 8, pages 353–356, and Volume 16, pages 562 et seq., and Lindner, Tenside, Textihilfsmittel, Waschrohstoffe, 2nd edition, Volume 1, pages 708–713, disclose the reaction of alkanes of more than 5 carbon atoms (individual paraffins) with chlorine, with or without sulfur dioxide, using thermal energy, with or without light energy, to give alkanes which are substituted by chlorine atoms and/or sulfochloride groups. As a rule, all theoretically possible isomers are formed in such reactions (Ullmann, Volume 8, page 354, 2nd paragraph. In addition to the isomers of the same degree of substitution, for example all isomers of monochloro-n-pentadecane, isomers of the progressive substitution stages, for example isomers of dichloro-, trichloro- and polychloro-n-pentadecane, are formed (as a result of over-chlorination or over-sulfochlorination), even though not all the starting paraffin has already reacted (Lindner, loc. cit., pages 710–713).

In industry the predominant practice is not to chlorinate or sulfochlorinate an individual alkane, but an alkane mixture (paraffin) in the form of paraffin waxes, cracking residues, oil-containing mixtures of solid paraffins encountered in lubricating oil fractions (slack wax), petroleum fractions, for example of boiling range from 250° to 350° C., hydrocarbons obtained from the Fischer-Tropsch synthesis, for example of boiling points from 195° to 330° C., and low molecular weight polyolefins. Hence, such reactions to a large extent produce, especially in the case of the conventional continuous processes (Lindner, loc. cit., pages 710–713), compounds which carry an excess of chlorine atoms or sulfochloride groups relative to the molar ratio of the reactants (polysubstituted compounds), whilst on the other hand a corresponding proportion of paraffin remains unconverted. The proportion of unconverted and polysubstituted paraffin present in the product of, for example, a continuous process can be as much as 70 percent by weight (calculated as starting paraffin), based on the total starting paraffin in the reaction mixture.

The content of unconverted paraffin in such mixtures is a particular disadvantage. This content tends to cloud the liquid, substituted paraffin, separates out in due course and interferes with the use of these paraffins and of their secondary products. To a lesser extent, the polysubstituted paraffins can also interfere with the eventual use of the product. For example they reduce the softening action, detergency and wetting of corresponding textile assistants, the lubricating action of synthetic lubricating oils and the emulsifying action of emulsifiers based on such chloroparaffins, and have an adverse effect on textiles treated with assistants based on such chloroparaffins. Similar remarks apply to the use of such products as fat liquors. If an isomer mixture of a particular degree of substitution, for example a mixture of monochloroalkanes, is required, its isolation, for example by distillation, is the more difficult, the higher is the proportion of the other components in the reaction mixture.

Process variants which seek to produce homogeneously substituted paraffins by appropriate temperature control or by using a shorter reaction time give an unsatisfactory yield of homogeneous end product, and, depending on the process, additional difficulties, for example dechlorination, dehydrochlorination, cracking, carbonization, explosive reaction or deposition of carbon, may occur (Ullmann, loc. cit., Volume 8, pages 354–355; Volume 5, pages 438 et seq.).

An improved process, wherein the reaction is carried out stepwise in several reaction vessels, is unsatisfactory, if only because it lacks simplicity of operation and economy. Chlorination with an excess of paraffin based on chlorine (ie. incipient chlorination), admittedly gives a lower proportion of polysubstituted compounds but a higher proportion of unconverted paraffin, which, for the reasons mentioned above, makes the further processing of the final mixture much more difficult still.

German Published Application DAS 2,217,530 relates to a process for the preparation of alkanes of more than 5 carbon atoms, which are substituted by chlorine atoms and/or sulfochloride groups, the number of substituents in the alkane molecule corresponding to the molar ratio of the starting materials, by reaction of alkanes with chlorine, or with chlorine and sulfur dioxide, by passing the alkanes, at a throughput of from 0.1 to 30 kilograms per hour per liter of reaction space, and chlorine or chlorine and sulfur dioxide at a throughput of from 0.1 to 20 kilograms per hour per liter of reaction space, upward through a reaction chamber of which the lengthwise axis forms an angle of from 1.5° to 70° with the horizontal, the velocity of the gas layer being from 2 to 30 meters per second and the residence time of the gas layer in the reaction chamber being from 2 to 60 seconds.

If, in contrast to this procedure, the reactants are passed downward through a reaction tube, the mixing of the liquid is less and the gaseous reactants react non-uniformly with the liquid. If the reactants are passed upward through a vertical tube, good mixing is admittedly achieved, but the upward movement of the liquid requires a very high gas velocity. Accordingly, as disclosed in German Published Application DAS 2,217,530, a very long tube is required, since, to achieve complete conversion, a certain minimum residence time of the reaction gases in the tube must be observed. It is true that if packings are used in the reaction tube to break up the liquid, higher conversions are achieved over a short reaction zone, but on carrying out the chlorination or sulfochlorination on an industrial scale it is not possible - as disclosed in German Published Application DAS No. 2,217,530, to remove the heat of reaction, generated within a relatively small space, in such a way as to maintain a uniform temperature in the reaction liquid and to avoid the above difficulties. DAS No. 2,217,530 also states that the reaction can be carried out with irradiation, the light source used being preferably any source emitting in the visible region. Light sources having a high proportion of their radiation in the wavelength range of from 300 to 500 nanometers are particularly preferred. The Examples show that each tube section of the spiral reaction chamber is irradiated with the same wavelength range. Compared to the above processes, this method gives the mixture of end products more simply and more economically, and with better space-time yield.

German Laid-Open Application DOS. No. 2,459,159 describes a similar reaction, in which a part of the reaction product leaving the reaction chamber is recycled to the reactor. In this process, again, the entire reaction chamber may be irradiated to the same wavelength range.

We have found that the process of German Published Application DAS No. 2,217,530 can be further improved if in the first part of the reaction chamber, which accounts for from 10 to 50 percent of the total length of the lengthwise axis of the reaction chamber, the reaction mixture is irradiated with light principally of wavelengths of from 500 to 700 nanometers, and in the remaining part of the reaction chamber the reaction mixture is irradiated with light principally of wavelengths of from 200 to 500 nanometers.

In an advantageous embodiment of the process, a tubular spiral consisting of several reaction tubes inclined to the horizontal and connected to one another by tubular bends is used, the spiral having a length: diameter ratio of from 100:1 to 10,000:1.

In a further advantageous embodiment of the process, the lengthwise axis of the total reaction chamber, or the individual reaction tubes and, if desired, the bends, forms or from an angle of from 1.5° to 30° with the horizontal.

In yet a further advantageous embodiment of the process, a part of the reaction mixture leaving the reaction chamber is recycled to the reaction.

If tetradecane is used, the reaction can be represented by the following equations:

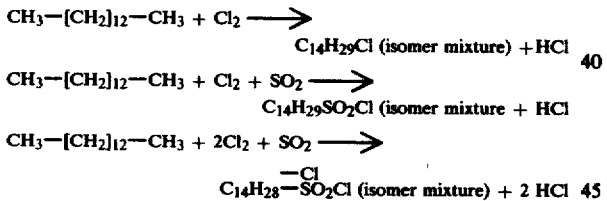

Compared to the conventional processes, the process according to the invention surprisingly gives chlorinated and/or sulfochlorinated alkanes, in which the number of substituents corresponds to the molar ratio of the starting materials, more simply and more economically, and with better space-time yield. The proportion of unconverted alkanes and of over-chlorinated and/or over-sulfochlorinated compounds is less, even in comparison with the processes of German Published Application DAS No. 2,217,530 and German Laid-Open Application DOS No. 2,459,159. Discolorations are not observed. All the difficulties, mentioned above, in further processing and in the use of the end products or secondary products and of the goods treated therewith are substantially reduced compared to the prior art processes. Further advantages of the process according to the invention are a more uniform reaction temperature and a substantially shorter reaction time. Furthermore, there is good heat transfer from the reaction mixture to the tube wall, which is important in ensuring simple and economical removal of the heat of reaction, especially at high throughputs. All these advantageous properties are surprising, especially in view of German Published Application DAS No. 2,217,530 and German Laid-Open Application DOS No. 2,459,159, since it would have been expected that on the same irradiation with the same wavelength range, especially at high throughputs, the heat of reaction would be more difficult to remove completely by cooling, so that overheating of the reaction product would occur or the reaction would take place incompletely. Furthermore, the process according to the invention surprisingly avoids, a priori, problems in the distribution of the reactants. Particles whose material exchange with the gas phase is favored compared to the bulk of the reaction mixture undergo less over-chlorination. Such particles, in the form of droplets and bubbles form throughout the reactor at the high flow rate employed. The process according to the invention thus surprisingly prevents the deposition of insoluble particles from the homogeneous final mixture.

Over-chlorinated particles are also a source of problems in the apparatus itself. In fact, it is hardly possible to prevent small amounts of the reaction mixture from leaving the reaction chamber as an aerosol or mist. If over-chlorinated products, which are solid at room temperature, are present therein, they lead to considerable problems in working up the off-gas, since they clog the pipelines. The sparingly soluble, highly chlorinated compounds can only be removed with great difficulty. Furthermore, in the known processes, the direct chlorination of the alkanes is undesirably favored when carrying out a sulfochlorination. In such cases, the process according to the invention has the surprising advantage that in spite of the high chlorine concentration in the gas phase the reaction takes place at a more moderate rate, no cooling problems arise, chlorination of the alkane, when carrying out a sulfochlorination, is not favored to a greater extent than usual, and the throughput is substantially increased without the presence of chlorine in the off-gas. The process according to the invention causes relatively less pollution of the environment.

The starting alkanes used are preferably those of 10 to 30, advantageously 14 to 24, especially 19 to 23, carbon atoms. They may be branched or straight-chain and may be used as individual compounds or, advantageously, as an alkane mixture. Examples of suitable alkanes are n-dodecane, n-tridecane, n-tetradecane, n-pentadecane, n-hexadecane, n-heptadecane, n-octadecane, n-nonadecane, n-eicosane, n-nonane, 2,2,3,3-tetramethylbutane, 2,2,4-trimethylpentane and n-triacontane. If only for economic reasons, the paraffins referred to in the prior art are generally used, in which case the carbon number depends on the paraffin employed; thus, the petroleum fractions used for the sulfochlorination preferably consist of mixtures of alkane isomers of various carbon numbers, the average being from 14 to 18 carbon atoms per molecule.

The starting materials may be employed in the stoichiometric amounts; for example, 4 moles of chlorine and 1 mole of sulfur dioxide may be used per mole of alkane to prepare trichloroalkane monosulfochlorides. In the case of alkane mixtures, such as the paraffins mentioned, the stoichiometric amounts relate to one mole of alkane having the average number of carbon atoms found for the particular paraffin. To prepare disubstituted, trisubstituted and more highly substituted alkanes and paraffins, it is preferred to use an excess of chlorine, with or without sulfur dioxide, based on the alkane or paraffin; it is possible to use amounts of chlorine in excess of the stoichiometric amount, namely of up to 130 percent by weight, advantageously of from 105 to 120 percent by weight, above the said amount, and, where relevant, of up to 200 percent by weight of sulfur dioxide over the stoichiometric amount, advantageously of from 110 to 170 percent by weight over the said amount. In the case of alkane mixtures or paraffins, the calculation is based on the average molecular weight. When preparing monosubstituted compounds, it is advantageous to use less than the stoichiometric amount of chlorine (incipient chlorination) and, where relevant, of sulfur dioxide; amounts of chlorine of down to 10 percent by weight, advantageously of from 20 to 50 percent by weight (based on the stoichiometric amount) may be used.

In the case of all the sulfochlorinations, the end products, or mixtures of end products, virtually always contain a small proportion of chlorine substituents in addition to the sulfochloride substituents. Accordingly, in addition to pure alkanesulfochlorides, isomer mixtures of chloroalkanesulfochlorides and chloroalkanes are formed. If this proportion of chlorine substituents is to be kept very low, a less than equivalent amount of chlorine, as stated above, is used, advantageously with a ratio of from 0.5 to 0.9, preferably from 0.6 to 0.8, mole of chlorine per mole of sulfur dioxide.

The process according to the invention is based on the observation that the compounds to be reacted must be introduced into the lower end of a tube inclined upward from the horizontal and that at the same time the gas velocity must be kept so high that the gas forces the liquid upward and the latter flows upward as a thin layer. We have found that following this procedure the liquid, which tends to flow backward, is caused to execute a wave-like, rolling upward motion as a result of the gas flowing over it, and undergoes thorough mixing without a detrimental amount of back-mixing occurring. The upward-moving liquid comes into uniform contact with the gas and assumes a uniform temperature. The liquid initially consists of the liquid alkanes or, where these are normally solid, of the alkane melt and is progressively converted to the end product, or mixture of end products, as it flows through the tube. Accordingly, the reaction takes place in a two-layer system, where the liquid is mixed thoroughly without substantial back-mixing. Over the entire reaction zone, the gas and the liquid remain in the form of a layer, that is to say complete mixing of gas and liquid, extending over the entire cross-section of the space, does not occur at any point of the reaction chamber. The mixing of gas and liquid which occurs is a surface mixing and there is no turbulent intermixing of the two layers.

It is preferred to use a throughput of from 0.1 to 25, especially from 0.1 to 20, kilogram of alkane and from 0.1 to 13, especially from 0.1 to 5, kilogram of chlorine, or chlorine and sulfur dioxide, per hour, per liter of reaction space, and to use velocities of the gas layer of from 2 to 30, especially from 3 to 10, meters per second, and of the liquid layer of from 0.02 to 3, especially from 0.03 to 1, meter per second. The preferred residence times are from 2 to 60, especially from 2 to 30, seconds in the case of the gas layer and from 60 to 1,200, especially from 180 to 900, seconds in the case of the liquid layer of the reaction mixture.

The reaction is in general carried out at from 20° to 160° C., under atmospheric or superatmospheric pressure, advantageously under a gas pressure of from 1 to 4, preferably from 1.2 to 2.5, atmospheres, batchwise or, preferably, continuously. The preferred reaction temperatures are from 60° to 160° C. in the case of chlorinations, from 20° to 40° C. in the case of sulfochlorinations and from 25° to 120° C., especially from 30° to 90° C., in the case of simultaneous chlorination and sulfochlorination. Organic solvents which are inert under the reaction conditions, such as chlorohydrocarbons, eg. carbon tetrachloride, tetrachloroethylene, tetrachloroethane or mixtures of these, may or may not be used; where they are used, suitable amounts are from 5 to 70 percent by weight, based on alkane or paraffin.

The reaction chamber selected is advantageously a tube having a length of from 10 to 100, preferably from 20 to 90, meters and an internal diameter of from 0.01 to 0.10, preferably from 0.015 to 0.08, meter. The lengthwise axis of the reaction chamber makes an angle of from 1.5° to 70°, preferably from 1.5° to 30°, with the horizontal. Advantageously, the reaction chamber consists of tubes in the form of a spiral. The total reaction space can also consist of a plurality of reaction chambers, advantageously in the form of tubes, which are connected in series, with all or some of the lengthwise axes of the individual chambers (tubes) forming an angle according to the invention with the horizontal, the angle varying from tube to tube. A smaller proportion of the chambers (tubes), accounting in general for from 0 to 20 percent of the total tube length, can also be horizontal, or be inclined to the horizontal at an angle of only from 0° to 1.5°, or of above 70°, though in general such chambers will not be inclined at an angle above 70°, but more advantageously at from 0° to 1.5° or, more particularly, will be horizontal; this smaller proportion of the chambers advantageously consists only of bends which connect the individual tubes, inclined to the horizontal at the angle according to the invention, with one another. In all these cases, the lengthwise axis of the total space corresponds to the line connecting the center points of the inlet and outlet cross-section of the total reaction chamber, advantageously of a tube constructed by assembling straight lengths of tube by means of bends, in the manner of a spiral staircase. For the purposes of the invention, bends means curved tube couplings. Each bend connects the outlet of one tube to the inlet of the next-adjoining tube, and all the tubes are inclined at an angle according to the invention, advantageously at the same angle, to the horizontal, whilst the bends a) are also inclined to the horizontal, advantageously at the same angle as the tubes, or b) for constructional reasons are at right angles to the tubes and run horizontally or c) more advantageously, correspond at the end of the bends to the angle of inclination of the adjoining tubes and run horizontally in the remaining, central part of the bend, as depicted in FIGS. 1 and 2 of the drawing, as described below. The preferred embodiment is a tubular reaction chamber in the shape of a spiral, spiral staircase or stair-well corresponding to this concept, with the individual straight lengths of tube corresponding to the individual sections of the staircase and each bend corresponding to the footpace which connects them. Accordingly the greater part, namely the central section, of each bend which connects the straightlengths of tube crosswise to one another advantageously runs horizontally or at an angle of inclination which is as a rule less than 70°, in general from 0 to 2°, always crosswise or horizontally to the direction of the lengths of tube, but never at right angles to the said direction, ie. the angle of inclination of each length of tube to the horizontal must not lie in one plane with the angle of inclination of the next length of tube to the horizontal. In this preferred embodiment of the spiral or spiral staircase, it is advantageous to use from 10 to 200 individual tubes and accordingly from 9 to 199 bends; preferably, the length:diameter ratio of the spiral (tubes and bends) is from 100:1 to 10,000:1, especially from 200 1 to 8,000:1. Advantageously, the bends have the same internal diameter as the reaction tubes, each bend or central portion of a bend has the same dimensions and angle of inclination as all the others, and/or all lengths of tube have the same dimensions and angle of inclination as all the others.

The heat of reaction can be removed by external water cooling of the tube system, for example by using jacketed tubes. Cooling can also be effected advantageously by means of a tube located concentrically in the interior of the reaction tube, with coolant flowing through this inner tube. Unlike the outer cooling tube, the inner cooling tube does not have to be transparent and can therefore consist of a metallic material, thereby simplifying the problem of cooling because of the higher heat transfer coefficient of a metallic material as compared to that of glass. Furthermore, fitting a concentric tube into the reaction tube assists the mixing and reaction of liquid with gas.

In a preferred embodiment, a part, preferably from 3 to 40 per cent by weight, especially from 5 to 20 per cent by weight, of the reaction mixture leaving the reaction chamber is recycled to the reaction and is again chlorinated, sulfochlorinated or chlorinated and sulfochlorinated, together with the fresh hydrocarbon. In respect of the recycling and reaction, the conditions and process characteristics described in German Laid-Open Application DOS No. 2,459,159 can advantageously be used. It has been found that continuous recycling of from 5 to 20 per cent of a sulfochlorination mixture suffices to ensure that after hydrolysis of the end products, materials having a very good wetting action are obtained. The wetting index is the time in seconds which a cotton disc of 30 mm diameter requires to sink in 200 ml of a solution containing 1 g of wetting agent. The foam index is less than 30 seconds. This is determined as follows: 0.5 g of substance is made up to 100 ml with sodium hydroxide solution of 20° Baume strength in a 250 ml shaking cylinder, and the mixture is then vigorously shaken 20 times in a vertical direction. The foam index is the latest time in seconds at which 5 ml of foam still remain.

The reaction is carried out with irradiation, the preferred sources for generating the light being any which emit in the visible region. For example, sunlight or artificial light, for example from quartz lamps, mercury vapor lamps, daylight lamps or fluorescent tubes may be used. Immersed lamps, round which the reaction mixture flows, may also be used. Advantageously, the desired wavelengths alone are employed for the irradiation, by combining the light source with appropriate filters. The entire reaction chamber (advantageously a tubular spiral) is irradiated, with the gas layer and liquid layer entering the reaction chamber being irradiated, in the first part (lower part) of the reaction chamber (tubular spiral) with light of which a high proportion is in the wavelength range of from 500 to 700, preferably from 530 to 680, nanometers, and thereafter, in the remaining second part (upper part) of the reaction chamber (tubular spiral), with light of which a high proportion is in the wavelength range of from 200 to 500, preferably from 330 to 460, nanometers. The total reaction space is divided along its total length, in such a way that the first part accounts for from 10 to 50, preferably from 20 to 40, per cent of the total length of the lengthwise axis of the reaction chamber, and the remaining, second part accordingly accounts for from 50 to 90, preferably from 60 to 80, per cent of the said total length. The proportion of the above wavelength ranges employed for irradiation accounts for more than 50 and up to 100 per cent of the total radiant intensity (light intensity); preferably, the wavelength range of from 500 to 700 nanometers accounts for from 60 to 100, especially from 80 to 100, per cent of the total radiant intensity (light intensity) in the first part of the reaction chamber, whilst the wavelength range of from 200 to 500 nanometers in the second part of the reaction chamber accounts for from 60 to 100, especially from 80 to 100, per cent of the total radiant intensity (light intensity), the total radiant intensity in each case referring to the light used in the particular part of the reactor. If desired, some parts which are difficult to irradiate, for example the space in the bends, may, in one or both parts of the reaction chamber, be left unirradiated, and such parts may in total account for from 0 to 25 per cent of the total length of the lengthwise axis of the total reaction space.

The reaction may be carried out as follows: the starting materials are passed, at the reaction temperature, the reaction pressure and the throughputs stated earlier, from below through the reaction chamber which is inclined to the horizontal, whilst irradiating the materials, in the first and second part, with light of the particular wavelengths according to the invention. Advantageously, the liquid reaction mixture leaving the reaction chamber is passed, together with the reaction gases, through a packed trickle tower downwards in co-current, in order to cause the reaction of any last remnant of starting material, for example chlorine, in the reaction gases. In the case of individual alkanes, the end product is isolated from the reaction mixture in the usual manner, for example by fractional distillation. In the majority of cases, particularly in industrial operation, mixtures of starting alkanes and hence mixtures of end products are involved; the latter can be purified by distillation but are in most cases directly processed further, for example by hydrolysis. For example, the sulfochlorination product is hydrolyzed with aqueous sodium hydroxide solution at 100° C., the mixture is cooled and the solid sodium chloride which has separated out is removed. This gives an alkali metal sulfonate solution which after addition of a few per cent of an antifoam agent constitutes an excellent wetting agent, which can be characterized in terms of the wetting index and foam index.

Figure 1:
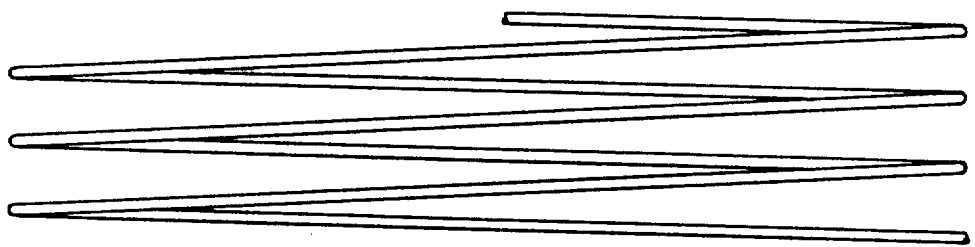
FIG. 1 is a side view of a spiral reaction tube arrangement in accordance with this invention.
Figure 2:
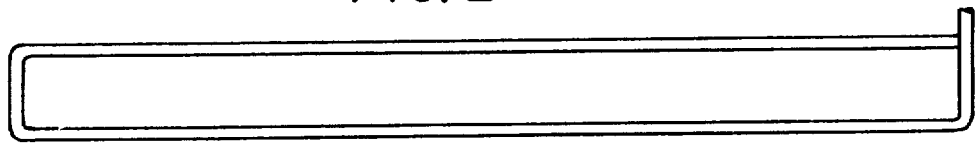
FIG. 2 is a view from above of one "level" of the spiral staircase.

FIGS. 1 and 2, taken together, depict the apparatus described in Example 1 below.

The substituted alkanes or paraffins obtainable by the process of the invention are pesticides, plasticizers, solvents and valuable starting materials for the preparation of such substances, as well as of fat liquors, wetting agents, detergents, lubricating oils, synthetic resins and slip agents. Regarding their use, reference may be made to the publications mentioned above and to Ullmanns Encyklopädie der technischen Chemie, Volume 5, pages 435, 437 and 448.

In the Examples which follow, parts are by weight.

EXAMPLE 1

(a) A slack wax is used which has the following average characteristics:

| | |
|---|---|
| mean chain length | $C_{21.2}H_{44.4}$ |
| mean molecular weight | 299 |
| melting point | $+41°$ C. |
| density at $45°$ | 0.765 |

Its percentage composition was as follows:

| Carbon number | Proportion in % by weight, based on total paraffin |
|---|---|
| $C_{12}-C_{15}$ | 0.3% |
| $C_{16}$ | 0.2% |
| $C_{17}$ | 1.1% |
| $C_{18}$ | 4.1% |
| $C_{19}$ | 11.2% |
| $C_{20}$ | 16.2% |
| $C_{21}$ | 19.2% |
| $C_{22}$ | 17.4% |
| $C_{23}$ | 14.1% |
| $C_{24}$ | 8.9% |
| $C_{25}$ | 4.5% |
| $C_{26}$ | 2.2% |
| $C_{27}$ | 0.6% |

120 parts of paraffin wax, in liquid form, and 94 parts of gaseous chlorine are introduced, per hour, into the lower end of a tube system of the following construction: 32 straight glass tubes each of 2 m length and 50 mm internal diameter are connected in the shape of a spiral by 31 bends of the same internal diameter, in the manner of a spiral staircase, the upward inclination of each tube being 2°, with the central portion of each bend running horizontally, whilst at the beginning and end of each bend there is a transition from 0 inclination to the 2° inclination of the adjoining tube. In total, the bends, having an inclination of from 0 to 1.5°, account for 11.3 per cent of the total tube length. In each tube there is concentrically located a second glass tube of external diameter 30 mm (internal diameter 24 mm), through which cooling water is passed. In this way, a reaction chamber of annular cross-section is formed, the width of the ring (clearance between the inner and outer shell) being 10 mm. Each of the lower 10 tubes is externally irradiated by means of a 60 watt fluorescent tube in which from 80 to 95 per cent of the total light intensity lies in the wavelength range of from 500 to 700 nanometers, whilst each of the 22 remaining, upper tubes is irradiated with a fluorescent tube of the same strength, in which from 80 to 95 per cent of the total light intensity lies in the wavelength range of from 300 to 500 nanometers. The bends are not irradiated, so that the non-irradiated proportion of the total tube length is 22.5 per cent. The gaseous mixture flows through the tube system at a throughput of 0.9 kilogram of chlorine per hour per liter of reaction space and forces the reaction liquid upward as a thin layer. The residence time of the gas in the tubular system is 10.1 seconds, whilst the residence time of the liquid is 6 minutes. The gas velocity is 8.32 m/sec. The throughput of liquid is 1.14 kilograms of alkane per hour per liter of reaction space. Whilst passing through the tubular reactor, the reaction mixture becomes heated by the heat of reaction which is liberated. The temperature is maintained at 75° C. After leaving the tubular system, the reaction liquid and reaction gas are passed into the upper part of a trickle tower which has a length of 1 m and a diameter of 150 mm and is filled with Raschig rings. The temperature of the reaction liquid does not rise in the trickle tower, which is not cooled. The liquid and gas are separated in a vessel located below the trickle column. Dissolved hydrogen chloride is then expelled from the reaction liquid by flushing with air.

Per hour, 166 parts of chloroparaffin containing 28.3 per cent by weight of chlorine are obtained. The yield, based on slack wax employed and on chlorine, is virtually quantitative in respect of paraffin which has been substituted in accordance with the molar ratio of the starting materials; the off-gas consists of chlorine-free hydrogen chloride. The final mixture is a water-white oily liquid which is homogeneous at room temperature, and remains clear and liquid on storage.

(b) (Comparison)

If the reaction is carried out continuously, in the conventional manner, following the method described by Lindner, Volume 1, pages 713, 2nd paragraph, the final mixture obtained has the same chlorine content, but on standing 10 per cent by weight of unconverted paraffin separates out as a solid. A corresponding proportion of polychloroparaffin has been formed and remains in solution.

(c) (Comparison)

If the tubular system is irradiated over its entire length with fluorescent tubes giving wavelengths of from 500 to 700 nanometers, only 80 parts of slack wax and 64 parts of gaseous chlorine can be passed through the system per hour. 110.5 parts per hour of chloroparaffin containing 28.3 per cent of chlorine are obtained; 1.4 parts per hour of chlorine remain in the off-gas. If the throughput is increased to 120 parts of slack wax and 94 parts of chlorine, more than 30 parts of chlorine per hour remain in the off-gas, and a homogeneous end product is not obtained.

EXAMPLE 2

(a) A paraffin of the following average characteristics is used:

| | |
|---|---|
| mean molecular weight | 215.25 |
| mean chain length | $C_{15.25}$ |
| boiling point 247.5–289.0° C. | |
| density at 20° 0.768 | |
| $n_D^{20} = 1.431$ | |

Its percentage composition was as follows:

| | |
|---|---|
| $C_8$ | 0.04% |
| $C_9$ | 0.02% |
| $C_{10}$ | 0.06% |
| $C_{11}$ | 1.73% |
| $C_{12}$ | 4.21% |
| $C_{13}$ | 7.63% |
| $C_{14}$ | 16.39% |
| $C_{15}$ | 25.20% |
| $C_{16}$ | 25.86% |
| $C_{17}$ | 15.07% |
| $C_{18}$ | 2.19% |
| $C_{19}-C_{25}$ | 1.60% |

Per hour, 120 parts of paraffin are reacted, by the method described in Example 1, with 101 parts of $Cl_2$ and 80.4 parts of $SO_2$, in accordance with the empirical equation:

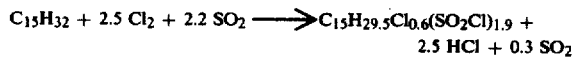

$$C_{15}H_{32} + 2.5\,Cl_2 + 2.2\,SO_2 \longrightarrow C_{15}H_{29.5}Cl_{0.6}(SO_2Cl)_{1.9} + 2.5\,HCl + 0.3\,SO_2$$

The reaction temperature is kept at 65° C. in the first 21 tubes, and at 45° C. in the remaining 11 tubes, by cooling with water passing through the concentric inner tubes. Per hour, 237 parts of a chlorinated, sulfochlorinated paraffin having a total chlorine content of 21 per cent are obtained, of which chlorine content 5 per cent is directly bonded to carbon atoms and the remainder (16 per cent) is bonded to the carbon chain via—SO₂—groups. The off-gas is free from chlorine. The yield of sulfochloride is virtually quantitative in respect of the paraffin which has been substituted in accordance with the molar ratio of the starting materials.

(b) (Comparison)

If the tubular system is irradiated over its entire length with fluorescent tubes giving wavelengths of from 500 to 700 nanometers, an hourly throughput of 80 parts of paraffin, 68 parts of chlorine and 60 parts of SO₂ gives only 158 parts of end product, having a total chlorine content of 21 per cent, of which 5 per cent is directly bonded to carbon atoms and the remainder (16 per cent) is bonded to the carbon chain via—SO₂—groups. Per hour, 24 parts of SO₂ and 1.8 parts of chlorine remain in the off-gas.

(c) (Comparison)

If the reaction chamber is irradiated over its entire length by means of lamps giving wavelengths of from 200 to 500 nanometers, local over-chlorination occurs at the surface and small droplets pass into the gas space. Precipitation occurs in the final mixture, and occasionally there are blockages in parts of the reaction chamber, and in the equipment used for working up.

EXAMPLE 3

(a) Per hour, 92.1 parts of paraffin of the composition stated in Example 2, 47.1 parts of gaseous chlorine and 120 parts of SO₂ are passed into the apparatus described in Example 1. After the tenth 2 meter tube, a further 31.5 parts per hour of chlorine are introduced. The temperature is kept at 45° C. in the inner tubes, by cooling with water. After leaving the tubular system, the liquid and gaseous reaction mixtures are passed into the upper part of a trickle tower which has a length of 1 m and a diameter of 150 mm and is filled with Raschig rings, and are then separated in a vessel located below the trickle column. From this vessel, 12 parts per hour of liquid reaction mixture (12 per cent by weight of the reaction mixture leaving the tubular system) are taken and pumped back into the lower end of the tubular reactor. The reaction mixture is freed from dissolved hydrogen chloride and from SO₂ by flushing with air. The yield, based on starting materials, is virtually quantitative in respect of paraffin which has been substituted in accordance with the molar ratio of the starting materials. Per hour, 180 parts of a chlorinated, sulfochlorinated paraffin having a total chlorine content of 21.9 per cent and a content of hydrolyzable chlorine of 14.8 per cent are obtained. The off-gas is free from chlorine. The end product is hydrolyzed with 130.5 parts of 50 per cent strength sodium hydroxide solution at 100° C., the hydrolyzed mixture is cooled to 15° C. and the sodium chloride which precipitates is separated off. 240 parts of an aqueous paraffinsulfonate solution are obtained which gives a foam index of 25 seconds and a wetting index of 10 seconds in sodium hydroxide solution of 10° Baumé strength, 23 seconds in sodium hydroxide solution of 20° Baumé strength and 44 seconds in sodium hydroxide solution of 30° Baumé strength.

(b) If the recycling of 12 parts per hour of sulfochlorination mixture to the reactor inlet is omitted, the results in respect of amount of end product are the same, but the wetting indices of the paraffinsulfonate solution are respectively 12 seconds/10° Baumé, 39 seconds/20° Baumé and 62 seconds/30° Baumé.

(c) (Comparison)

If the tubular system is irradiated, over its entire length, with fluorescent tubes giving wavelengths of from 500 to 700 nanometers, the reaction of the paraffin with chlorine and SO₂ is incomplete and the off-gas contains more than 20 parts per hour of chlorine.

(d) (Comparison)

If the tubular system is irradiated over its entire length with fluorescent tubes giving wavelengths of from 200 to 500 nanometers, the same problems as in Example 2c) are encountered.

We claim:

1. A process for the preparation of alkanes of more than 5 carbon atoms, which are substituted by chlorine atoms and/or sulfochloride groups, the number of substituents in the alkane molecule corresponding to the molar ratio of the starting materials, by the method of preparation of such compounds by reaction of alkanes with chlorine, or with chlorine and sulfur dioxide, by passing the alkanes, at a throughput from 0.1 to 30 kilograms per hour per liter of reaction space, and chlorine or chlorine and sulfur dioxide at a throughput of from 0.1 to 20 kilograms per hour per liter of reaction space, upward through a reaction chamber of which the lengthwise axis forms an angle of from 1.5 to 70° with the horizontal, the velocity of the gas layer being from 2 to 30 meters per second and the residence time of the gas layer in the reaction chamber being from 2 to 60 seconds, wherein, in the first part of the reaction chamber, which accounts for from 10 to 50 per cent of the total length of the lengthwise axis of the reaction chamber, the reaction mixture is irradiated with light principally of wavelengths of from 500 to 700 nanometers, and in the remaining part of the reaction chamber the reaction mixture is irradiated with light principally of wavelengths of from 200 to 500 nanometers.

2. A process as claimed in claim 1, wherein a tubular spiral consisting of several reaction tubes inclined to the horizontal and connected to one another by tubular bends is used, the spiral having a length: diameter ratio of from 100:1 to 10,000:1.

3. A process as claimed in claim 1, wherein the lengthwise axis of the reaction chamber, or the reaction tubes and, if desired, the bends, forms or form an angle of from 1.5 to 30° with the horizontal.

4. A process as claimed in claim 1, wherein a part of the reaction mixture leaving the reaction chamber is recycled to the reaction.

5. A process as claimed in claim 1, wherein the reaction is carried out with starting alkanes of 10 to 30 carbon atoms.

6. A process as claimed in claim 1, wherein the reaction is carried out with an excess of chlorine, over the stoichiometric amount, of from 105 to 120% by weight.

7. A process as claimed in claim 1, wherein the reaction is carried out with an excess of sulfur dioxide, over the stoichiometric amount, of from 110 to 170% by weight.

8. A process as claimed in claim 1, wherein the reaction in the case of the preparation of monosubstituted compounds, is carried out with amounts of chlorine below the stoichiometric amount, namely from 20 to 50% by weight of chlorine, and with a ratio of from 0.5 to 0.9 mole of chlorine per mole of sulfur dioxide.

9. A process as claimed in claim 1, wherein the reaction is carried out with a throughput of from 0.1 to 25 kilograms of alkane and from 0.1 to 5 kilograms of chlorine or chlorine and sulfur dioxide per hour per liter of reaction space, and with a velocity of the gas layer of from 2 to 30 meters per second.

10. A process as claimed in claim 1, wherein the reaction is carried out with a residence time of from 2 to 60 seconds for the gas layer and from 60 to 1,200 seconds for the liquid layer of the reaction mixture.

11. A process as claimed in claim 1, wherein the reaction is carried out at from 20 to 160° C.

12. A process as claimed in claim 1, wherein the reaction, in the case of a chlorination, is carried out at from 60 to 160° C.

13. A process as claimed in claim 1, wherein the reaction, in the case of sulfochlorination, is carried out at from 20 to 40° C.

14. A process as claimed in claim 1, wherein the reaction, in the case of a simultaneous chlorination and sulfochlorination, is carried out at from 25 to 120° C.

15. A process as claimed in claim 1, wherein the reaction is carried out under a gas pressure of from 1 to 4 atmospheres.

16. A process as claimed in claim 1, wherein the reaction is carried out in the presence of from 5 to 70% by weight, based on alkane or paraffin, of an organic solvent which is inert under the reaction conditions.

17. A process as claimed in claim 1, wherein the reaction is carried out in tubes of from 10 to 100 meters length and from 0.01 to 0.10 meter diameter.

18. A process as claimed in claim 1, wherein the reaction is carried out in a reaction chamber which is divided so that the first part corresponds to from 20 to 40 per cent of the total length of the lengthwise axis of the reaction chamber and the remaining, second, part corresponds to from 60 to 80 per cent of the said total length.

* * * * *